United States Patent
Khan et al.

(10) Patent No.: US 7,343,943 B2
(45) Date of Patent: Mar. 18, 2008

(54) MEDICATION DOSE UNDERFILL DETECTION SYSTEM AND APPLICATION IN AN AUTOMATED SYRINGE PREPARING SYSTEM

(75) Inventors: Abdul Wahid Khan, Lindenhurst, IL (US); Abdolhosein Nasiri, Ormond Beach, FL (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 502 days.

(21) Appl. No.: 10/944,438

(22) Filed: Sep. 17, 2004

(65) Prior Publication Data

US 2005/0252574 A1    Nov. 17, 2005

Related U.S. Application Data

(63) Continuation-in-part of application No. 10/846,959, filed on May 13, 2004, now Pat. No. 7,163,035.

(51) Int. Cl.
B65B 1/30    (2006.01)

(52) U.S. Cl. .............................. 141/95; 141/2; 141/27; 141/83; 141/329

(58) Field of Classification Search .................... 141/2, 141/18, 27, 83, 94, 95, 329; 73/293
See application file for complete search history.

(56) References Cited

U.S. PATENT DOCUMENTS

| | | | |
|---|---|---|---|
| 2,880,723 A | 4/1959 | Adams | |
| 2,981,432 A | 4/1961 | Flood | |
| 3,527,017 A | 9/1970 | Taylor et al. | |
| 3,736,933 A | 6/1973 | Szabo | |
| 3,807,467 A | 4/1974 | Tascher et al. | |
| 3,835,897 A | 9/1974 | Gess | |
| 3,865,236 A | 2/1975 | Rycroft | |
| 3,880,211 A | 4/1975 | Gess | |
| 4,501,306 A | 2/1985 | Chu et al. | |
| 4,535,820 A | 8/1985 | Raines | |
| 4,624,148 A | 11/1986 | Averette | |

(Continued)

FOREIGN PATENT DOCUMENTS

JP    2002340808    11/2002

(Continued)

OTHER PUBLICATIONS

B. Braun Medical Inc., product descriptions from on-line catalog, 3-pages.

*Primary Examiner*—Timothy L. Maust
(74) *Attorney, Agent, or Firm*—Darby & Darby P.C.

(57) ABSTRACT

An automated system is provided and includes a safety and cost reducing feature that is capable of detecting whether an underfill condition exists within the product container as a unit dose of medication is delivered thereto. More specifically, the medication is typically injected into the product container under action of a delivery device, such as a pump, and the underfill detection device is capable of calculating if air (air bubbles) has been dispensed into the product container and based on this information, the device is able to measure the amount of the unit dose of medication within the product container and if necessary, additional medication can be added if it is determined that an underfill condition exists in order to compensate for the presence of the air bubbles.

32 Claims, 8 Drawing Sheets

U.S. PATENT DOCUMENTS

| | | |
|---|---|---|
| 4,683,916 A | 8/1987 | Raines |
| 5,012,845 A | 5/1991 | Averette |
| 5,125,748 A | 6/1992 | Bjornson et al. |
| 5,256,154 A | 10/1993 | Liebert et al. |
| 5,341,854 A | 8/1994 | Zezulka et al. |
| 5,356,393 A | 10/1994 | Haber et al. |
| 5,597,530 A | 1/1997 | Smith et al. |
| 5,651,775 A | 7/1997 | Walker et al. |
| 5,704,921 A | 1/1998 | Carilli |
| 5,805,454 A | 9/1998 | Valerino |
| 5,899,889 A | 5/1999 | Futagawa et al. |
| 5,911,252 A | 6/1999 | Cassel |
| 6,027,472 A | 2/2000 | Kriesel et al. |
| 6,048,086 A | 4/2000 | Valerino |
| 6,915,823 B2 | 7/2005 | Osborne et al. |
| 6,991,002 B2 | 1/2006 | Osborne et al. |
| 7,017,622 B2 | 3/2006 | Osborne et al. |
| 2002/0020459 A1 | 2/2002 | Baldwin |
| 2002/0198738 A1 | 12/2002 | Osborne |
| 2004/0088951 A1 | 5/2004 | Baldwin |
| 2005/0045242 A1 | 3/2005 | Osborne et al. |
| 2005/0224137 A1 | 10/2005 | Tribble |

FOREIGN PATENT DOCUMENTS

| | | |
|---|---|---|
| WO | WO-2004/050038 | 6/2004 |

MEDICATION DOSE UNDERFILL DETECTION SYSTEM AND APPLICATION IN AN AUTOMATED SYRINGE PREPARING SYSTEM

CROSS-REFERENCE TO RELATED APPLICATION

This patent application is a continuation-in-part of U.S. patent application Ser. No. 10/846,959, filed May 13, 2004, now U.S. Pat. No. 7,163,035 which is incorporated herein by reference in its entirety.

TECHNICAL FIELD

The present invention relates generally to medical and pharmaceutical equipment, and more particularly, to an automated medication preparation that includes preparation of a unit dose of medication from a medication source and then delivery of the unit dose of medication to a product container, such as a syringe or the like, along with a device that is capable of detecting when an underfill condition exists in the product container.

BACKGROUND

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, including a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

A conventional syringe includes a barrel having an elongated body that defines a chamber that receives and holds a medication that is disposed at a later time. The barrel has an open proximal end with a flange being formed thereat and it also includes an opposing distal end that has a barrel tip that has a passageway formed therethrough. An outer surface of the barrel tip or luer can include features to permit fastening with a cap. Most often, the medication is contained within the chamber in a liquid state even though the medication initially may have been in a solid state, which was processed into a liquid state. The syringe further includes a plunger that is removably and adjustably disposed within the barrel.

Typically, a drug is provided of the shelf in solid form within an injectable drug vial that is initially stored in a drug cabinet or the like. To prepare an injectable unit dose of medication, a prescribed amount of diluent (water or some other liquid) is added to the vial to cause the solid drug to go completely into solution. Mixing and agitation of the vial contents is usually required. This can be a time consuming and labor intensive operation since first it must be determined how much diluent to add to achieve the desired concentration of medication and then this precise amount needs to be added and then the vial contents need to be mixed for a predetermined time period to ensure that all of the solid goes into solution. Thus, there is room for human error in that the incorrect amount of diluent may be added, thereby producing medication that has a concentration that is higher or lower than it should be. This can potentially place the patient at risk and furthermore, the reconstitution process can be very labor intensive since it can entail preparing a considerable number of medication syringes that all can have different medication formulations. This also can lead to confusion and possibly human error.

If the medication needs to be reconstituted, the medication initially comes in a solid form and is contained in an injectable drug vial and then the proper amount of diluent is added and the vial is agitated to ensure that all of the solid goes into solution, thereby providing a medication having the desired concentration. The drug vial is typically stored in a drug cabinet or the like and is then delivered to other stations where it is processed to receive the diluent. As is known, the drug vial typically includes a pierceable septum that acts as a seal and prevents unwanted foreign matter from entering into the drug vial so as to contaminate the contents thereof as well as keeping the contents safely within the interior of the drug vial when the drug is stored or even during an application. The septum is typically formed of a rubber material that can be pierced by a sharp transfer device to permit communication with the interior of the drug vial and then when the transfer device is removed the small piercing hole seals itself due to the material properties of the septum.

Typically, the medication is aspirated or otherwise withdrawn from the drug vial into a fluid conduit that can be in the form of a section of tubing or can be a cannula or a syringe. Unfortunately, one of the side effects that can occur when the medication is aspirated is that unwanted foreign particles or air bubbles or the like can be aspirated along with the medication into the fluid conduit. For example, the foreign particles can be in the form of particles of undissolved drug, dislodged particles of the septum, or any other foreign matter that may have found its way into the drug vial. Since the aspirated drug is intended for use in an application to a patient, the unwanted foreign matter can potentially pose a safety risk or at the very least is a sign of contamination of the drug delivery process and can raise other issues about the overall reliability. In addition, a unit dose of medication is carefully measured out for the patient and therefore, the presence of foreign matter reduced the overall volume of drug that is measured and delivered to the patient. In other words, the actual amount of drug that is dispensed is less than the apparent amount that is aspirated due to the presence of the foreign matter. Moreover and at the very least, the presence of foreign matter constitutes a contamination of the unit dose and often requires that the unit dose be discarded. This results in waste of the drug and increases the overall cost of the drug.

Moreover, another undesirable condition that can result in a number of the filled product containers being rejected as not being suitable for use is that during the filling of the product container, excess air is sometimes dispensed into the product container in contrast to fluid. This is undesirable since it results in the filled product container not containing the prescribed, selected amount of fluid (medication) as a result of the presence of excess air in the filled product container. The presence of air reduces the volume of the medication that is actually contained within the product container. This condition is not acceptable since the product container needs to have a precise amount of medication contained therein and if there is not enough medication contained therein due to the presence of excess air, then the product container must be rejected. This results in waste of perfectly good medication.

What is needed in the art and has heretofore not been available is a system and method for automating the medication preparation process and more specifically, a safety and cost reducing feature that is capable of detecting whether an underfill condition exists within the product container.

SUMMARY

In one exemplary embodiment, an automated medication preparation is provided and typically involves the preparation and dispensing of drug products, whether they are in a bag, a syringe or via some other type of administration vehicle. For example, in one embodiment the automated medication preparation is incorporated into a hood within an I.V. room and is constructed to be accessed in the course of manual preparation of an I.V. product, in order to ensure that the correct drug, dose, expiration and lot of a product are chosen.

In another embodiment, the system includes an automated device for delivering a prescribed unit dose of medication to the syringe by delivering the medication through an uncapped barrel of a syringe. This is preferably done in a just-in-time for use manner. One exemplary automated device for delivering a prescribed unit dose of medication to the syringe is in the form of an automated device having a fluid delivery device that is movable in at least one direction. The fluid delivery device is adapted to perform the following operations: (1) receiving and discharging diluent from a diluent supply in a prescribed amount to reconstitute the medication in a drug vial; and (2) aspirating and later discharging reconstituted medication from the drug vial into the syringe.

The system further includes a sensor for detecting any foreign matter (e.g., undissolved drug, pieces of septum, etc.) present in the reconstituted unit dose of drug prior to transfer of the reconstituted drug (unit dose) to the syringe. If foreign matter is detected, then the reconstituted drug is prevented from being delivered to the syringe, otherwise, the reconstituted drug is delivered to the syringe.

In yet another aspect of the present invention, the automated system includes a safety and cost reducing feature that is capable of detecting whether an underfill condition exists within the product container. More specifically, the medication is typically injected into the product container under action of a delivery device, such as a pump, and the underfill detection device is capable of calculating the amount of air (volume) that has been drawn into the aspiration line and then later dispensed into the product container and based on this information, the device is able to measure the amount of the unit dose of medication that is actually delivered to the product container and if necessary, additional medication can be added if it is determined that an underfill condition exists.

Further aspects and features of the exemplary automated safety cap removal mechanism disclosed herein can be appreciated from the appended Figures and accompanying written description.

DETAILED DESCRIPTION OF PREFERRED EMBODIMENTS

Figure 1:
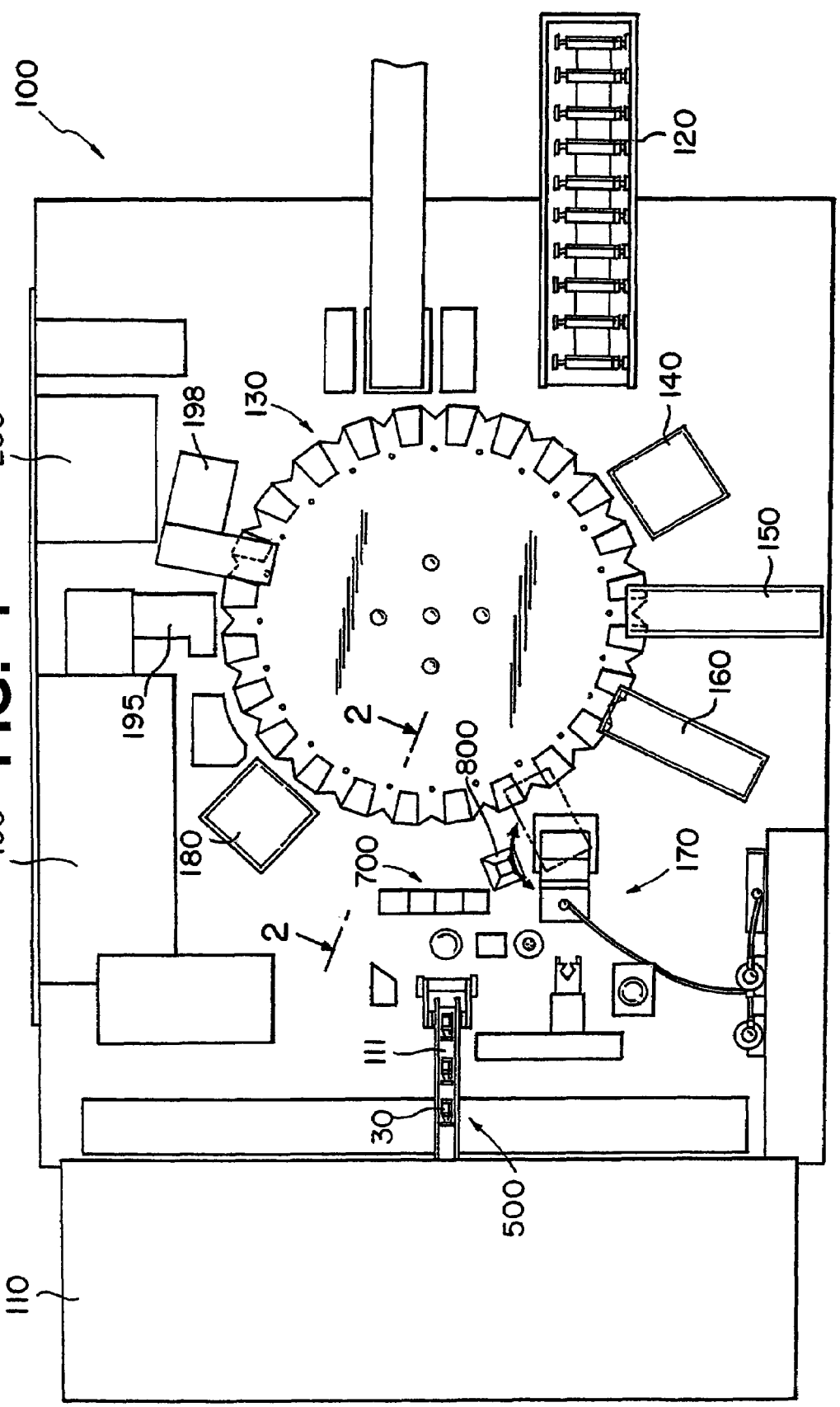
FIG. 1 is a diagrammatic plan view of an automated system for preparing a medication to be administered to a patient.

It will be understood that the present automated medication preparation disclosed herein can take any number of different forms that can equally be used with the vision system of the present invention. Thus, while a number of different applications are described herein, these applications are merely exemplary in nature and are not limiting in any way since it will be understood that other automated medication preparation systems can equally be used. In other words, one class of exemplary automated medication preparation typically involves the preparation and dispensing of drug products, whether they are in a bag, a syringe or via some other type of administration vehicle. For example, in one embodiment the automated medication preparation is incorporated into a hood within an I.V. room and is constructed to be accessed in the course of manual preparation of an I.V. product. In another embodiment, that is described in great detail herein and set forth in the drawing figures, the automated medication preparation system involves the automated preparation of a syringe in which the desired medication is stored. Thus, it will be broadly understood that the present invention covers a vision system used in combination with an automated medication preparation system that includes the preparation and dispensing of a drug product (unit dose of medication). Therefore, it will be understood that as used herein, a drug vial is merely one exemplary type of drug container, while a syringe is one exemplary type of drug product container and neither is limiting of the present invention.

FIG. 1 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc. under proper storage conditions. Typically, medications and the like are stored in sealed containers, such as vials, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at the first station 120 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150. At this point, the syringe is ready for use.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to a fourth station 160 using an automated mechanism, such a robotic gripping device as will be described in greater detail. At the fourth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station (fluid transfer station) 170 for injecting or delivering a diluent into the medication contained in the sealed container and then subsequently mixing the medication and the diluent to form the medication composition that is to be disposed into the prepared syringe. At this fluid transfer station, the prepared medication composition is withdrawn from the container (i.e., vial) and is then delivered into the syringe. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent if necessary or desired. The tip cap is then placed back on the syringe at a sixth station 180. A seventh station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200. The various devices that form a part of the system 100 as well as a detailed explanation of the operations that are performed at each station are described in greater detail in U.S. patent application Ser. Nos. 10/728,371; 10/426,910; 10/728,364; and 10/728,363 as well as International patent application Serial No. PCT/US03/38581, all of which are hereby incorporated by reference in their entirety.

Figure 4:
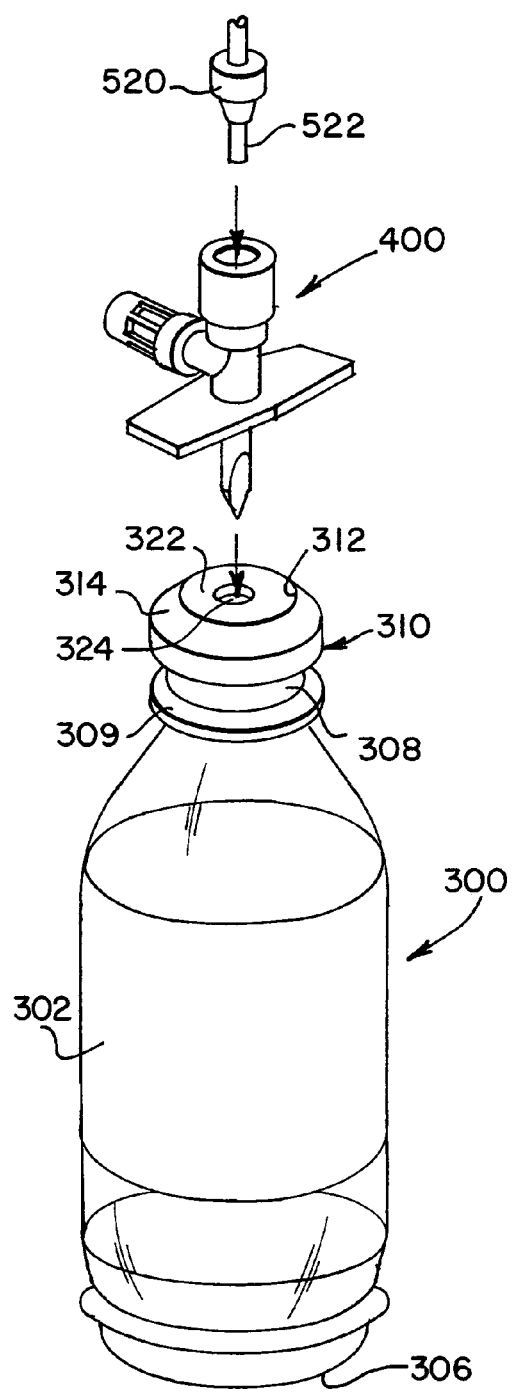
FIG. 4 is a perspective view of a drug vial and a fluid transfer device (dispensing pin) according to a first embodiment.
Figure 5:
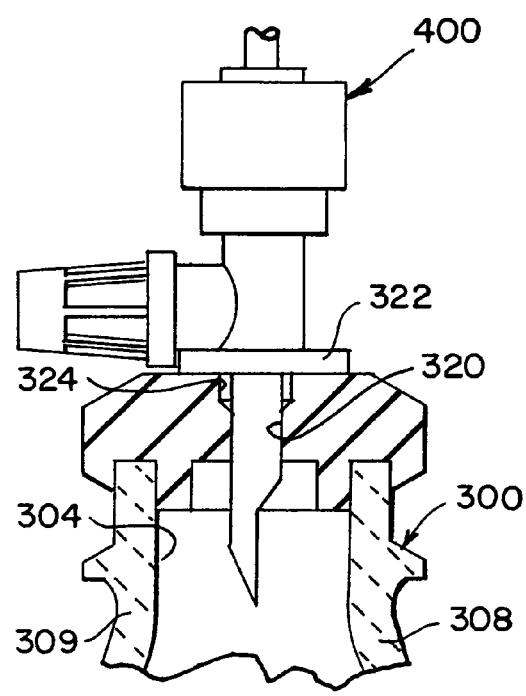
FIG. 5 is a cross-sectional view of the fluid transfer device of FIG. 4 being sealingly mated with a septum of the drug vial.

FIGS. 4-5 show one type of drug vial 300 that in its simple terms is a drug container that has a vial body 302 for storing a drug and a cap member or some other type of closure element 310 that is sealingly mated to an open end 304 of the drug container 300 opposite a closed end 306. The cap member 310 can be releasably attached to the open end 304 or it can be permanently attached after the contents are disposed within the vial body 302. The vial body 302 is preferably made of a transparent material so that the contents therein are visible, with one preferred material being glass. The illustrated drug vial 300 has a neck portion 308 near the open end 304 that tapers inwardly from a lower section of the vial body 302 such that the open end 304 has a diameter that is less than a diameter of the closed end 306. The neck portion 308 can also include an annular flange 309 that extends therearound and can be used to assist an individual or a robot that is part of an automated system in grasping and holding the drug vial 300 and moving it from one location to another one. In addition, the open end 304 itself can include an annular flange member 303 that is formed thereat to assist in attaching the cap member 310 to the vial body 302 as explained below.

The illustrated cap member 310 is of the type that includes a central opening 312 formed therethrough. As shown, the central opening 312 is preferably a circular opening that it formed over the opening of the end 304 of the vial body 302. This permits the contents in the vial body 302 to selectively travel through open end 304 and through the central opening 312. The exemplary cap member 310 is made of a metal material and can be crimped onto or otherwise attached to the annular flange member 303 at the open end 302 such that a peripheral planar top surface 314 that is formed around and defines the central opening 312 is disposed over the opening at end 304.

The drug vial 300 also includes a pierceable septum 320 that is at least partially disposed within the vial body 302 and more particularly within the open end 304. The pierceable septum 320 can be in the form of a rubber stopper that is generally hollow and includes a top surface 322 of reduced thickness to permit a cannula or the like to easily pierce the top surface of the septum 320. Once the top surface 322 is pierced, the member that pierces the surface can communicate directly with the interior of the vial body 302 and more particularly can be placed into contact with the contents in the vial body 302 for the purpose of withdrawing the contents or in the case where the cannula is used to inject a fluid into the vial body 302, the piercing member merely needs to pierce the septum 320 and be placed within the vial body 302. To create an even more easily pierceable top surface, the top surface 322 can include a recessed portion 324 (e.g., a dimple) that that is of reduced thickness relative to the surrounding portions of the septum 320. Optionally, a fluid transfer device 400 can be securely received in and attached to the drug vial 300 to facilitate fluid mating between the fluid delivery device and the drug vial 300. One type of fluid transfer device 400 is a dispensing pin and is described in great detail in Applicants' U.S. patent application Ser. No. 10/821,268; entitled DEVICE FOR RECONSTITUTING A DRUG VIAL AND TRANSFERRING THE CONTENTS TO A SYRINGE IN AN AUTOMATED MATTER, which is hereby incorporated by reference in its entirety.

Figure 2:
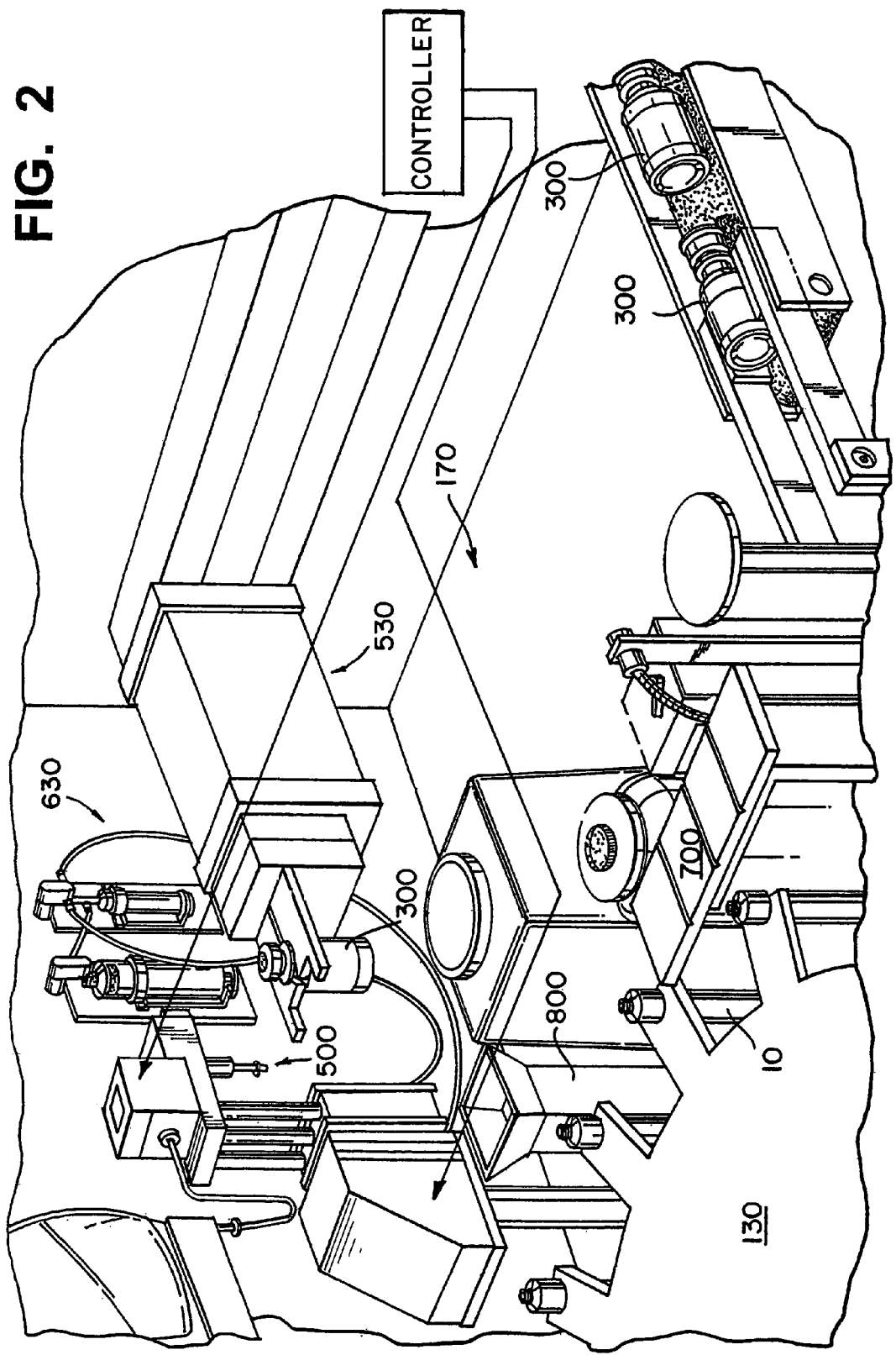
FIG. 2 is perspective view of a number of stations, including a fluid transfer station, that form a part of the automated system of FIG. 1.
Figure 3:
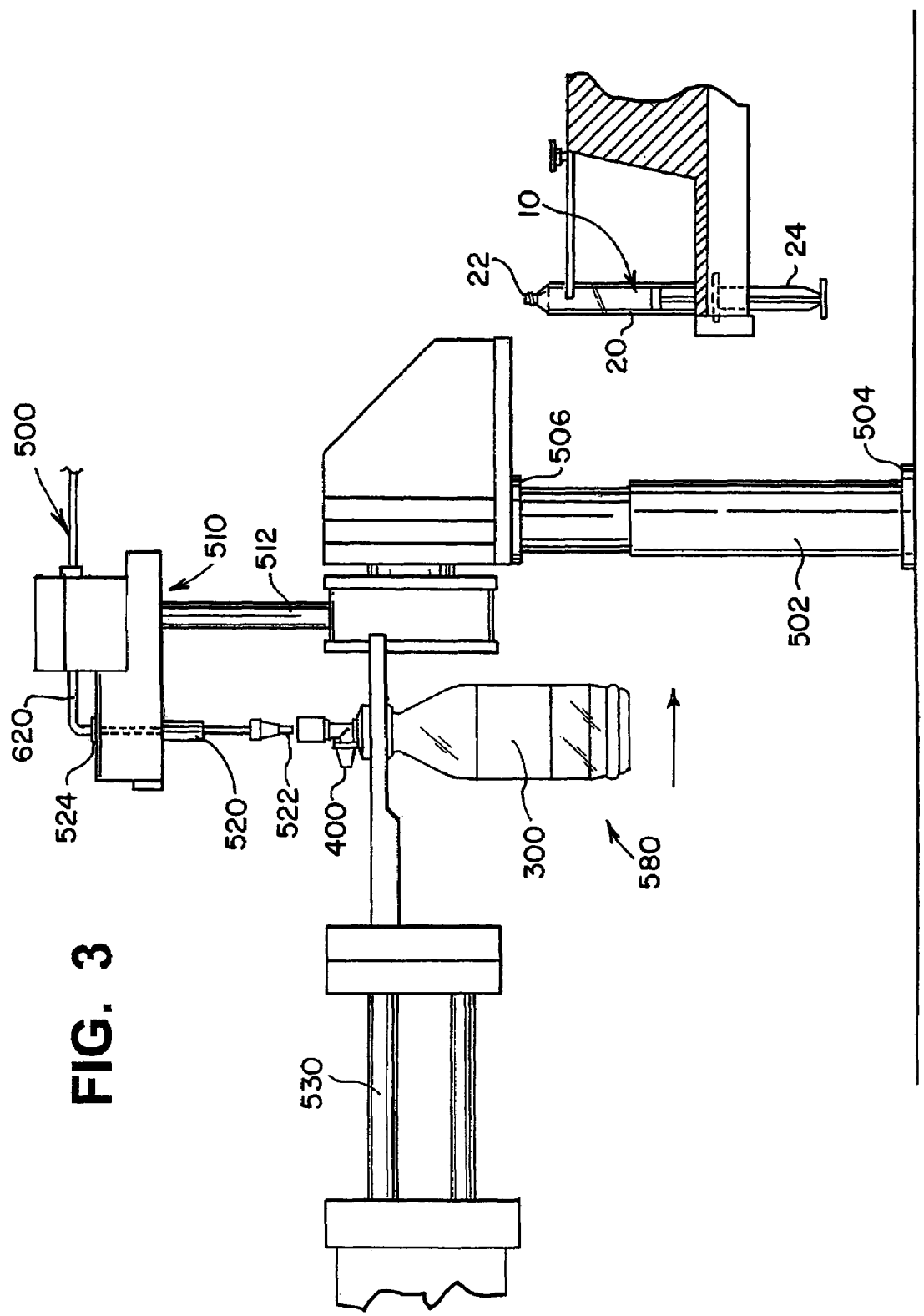
FIG. 3 is a side elevation view of a fluid transfer device in a first position where a fluid delivery system is in a retracted position and a vial gripper device moves the vial into a fluid transfer position.

FIGS. 2 through 11 illustrate parts of the fluid transfer station 170 for preparing the syringe for later use in which the transfer device 400 is used in the delivery and/or withdrawal of fluid from the vial 300. As shown in FIGS. 2-3, one exemplary cannula unit 500 can include a vertical housing 502 that is rotatably coupled to a base 504 between the ends thereof. At an upper end 506 of the housing 502, a cannula housing 510 is operatively coupled thereto such that the cannula housing 510 can be independently moved in a controlled up and down manner so to either lower it or raise it relative to the drug vial 300, and more particularly, relative to the transfer device 400, in the fluid transfer position. For example, the cannula housing 510 can be pneumatically operated and therefore, can include a plurality of shafts 512 which support the cannula housing 510 and extend into an interior of the vertical housing 502 such that when the device is pneumatically operated, the shafts 512 can be driven either out of or into the housing 502 resulting in the cannula housing 510 either being raised or lowered, respectively.

At one end of the cannula housing 510 opposite the end that is coupled to the vertical housing 502, the cannula housing 510 includes a cannula 520. The cannula 520 has a distal end 522 that serves to interact with the transfer device 400 for delivering or withdrawing fluid from the drug vial 300 and an opposite end 524 that is operatively coupled to a fluid source, such as a diluent, via tubing or the like. Instead of a cannula or the like, the housing 510 can contain and hold in place a section of fluid conduit (tubing) with a luer fitting or some other type of fitting at the end.

A robotic device 530 then advances forward to a fluid transfer station 530. The fluid transfer station 530 is an automated station where the medication (drug) can be processed so that it is in a proper form for injection into one of the syringes 10 that is coupled to the rotary dial 130. When the vial 300 contains only a solid medication and it is necessary for a diluent (e.g., water or other fluid) to be added to liquify the solid, this process is called a reconstitution process. Alternatively and as will be described in detail below, the medication can already be prepared and therefore, in this embodiment, the fluid transfer station is a station where a precise amount of medication is simply aspirated or withdrawn from the vial 300 and delivered to the syringe 10.

The precise steps of a reconstitution process and of an aspiration process using the cannula unit 500 are described in great detail in the previously incorporated U.S. patent applications which are assigned to the present assignee.

The cannula unit 500 includes a fluid delivery system 600 which includes a main conduit 620 that is operative coupled to the cannula 520 for delivering fluid thereto in a controlled manner, with an opposite end of the main conduit 620 being connected to a fluid pump system 630 that provides the means for creating a negative pressure in the main conduit 620 to cause a precise amount of fluid to be withdrawn into the cannula 520 and the main conduit 620 as well as creating a positive pressure in the main conduit 620 to discharge the fluid (either diluent or medication) that is stored in the main conduit 620 proximate the cannula 520. In the illustrated embodiment, particularly shown in FIG. 10, the fluid pump system 630 includes a first syringe 632 and a second syringe 634, each of which has a plunger or the like 638 which serves to draw fluid into the syringe or expel fluid therefrom. The main difference between the first and second syringes 632, 634 is that the amount of fluid that each can hold. In other words, the first syringe 632 has a larger diameter barrel and therefore has increased holding capacity relative to the second syringe 634. As will be described in detail below, the first syringe 632 is intended to receive and discharge larger volumes of fluid, while the second syringe 634 performs more of a fine tuning operation in that it precisely can receive and discharge small volumes of fluid.

The syringes 632, 634 are typically mounted so that an open end 636 thereof is the uppermost portion of the syringe and the plunger 638 is disposed so that it is the lowermost portion of the syringe. Each of the syringes 632, 634 is operatively connected to a syringe driver, generally indicated at 640, which serves to precisely control the movement of the plunger 638 and thus precisely controls the amount (volume) of fluid that is either received or discharged therefrom. More specifically, the driver 640 is mechanically linked to the plunger 638 so that controlled actuation thereof causes precise movements of the plunger 638 relative to the barrel of the syringe. In one embodiment, the driver 640 is a stepper motor that can precisely control the distance that the plunger 638 is extended or retracted, which in turn corresponds to a precise volume of fluid being aspirated or discharged. Thus, each syringe 632, 634 has its own driver 640 so that the corresponding plunger 638 thereof can be precisely controlled and this permits the larger syringe 632 to handle large volumes of fluid, while the smaller syringe 634 handles smaller volumes of fluid. As is known, stepper motors can be controlled with a great degree of precision so that the stepper motor can only be driven a small number of steps which corresponds to the plunger 638 being moved a very small distance. On the other hand, the stepper motor can be driven a large number of steps which results in the plunger 638 being moved a much greater distance. The drivers 640 are preferably a part of a larger automated system that is in communication with a master controller that serves to monitor and control the operation of the various components. For example, the master controller calculates the amount of fluid that is to be either discharged from or aspirated into the cannula 520 and the main conduit 620 and then determines the volume ratio as to how much fluid is to be associated with the first syringe 632 and how much fluid is to be associated with the second syringe 634. Based on these calculations and determinations, the controller instructs the drivers 640 to operate in a prescribed manner to ensure that the precise amount of volume of fluid is either discharged or aspirated into the main conduit 620 through the cannula 520.

The open end 636 of each syringe 632, 634 includes one or more connectors to fluidly couple the syringe 632, 634 with a source 650 of diluent and with the main conduit 620. In the illustrated embodiment, the first syringe 632 includes a first T connector 660 that is coupled to the open end 636 and the second syringe 634 includes a second T connector 662 that is coupled to the open end 636 thereof. Each of the legs of the T connectors 660, 662 has an internal valve mechanism or the like 670 that is associated therewith so that each leg as well as the main body that leads to the syringe itself can either be open or closed and this action and setting is independent from the action at the other two conduit members of the connector. In other words and according to one preferred arrangement, the valve 670 is an internal valve assembly contained within the T connector body itself such that there is a separate valve element for each leg as well as a separate valve element for the main body. It will be appreciated that each of the legs and the main body defines a conduit section and therefore, it is desirable to be able to selectively permit or prevent flow of fluid in a particular conduit section.

In the illustrated embodiment, a first leg 661 of the first T connector 660 is connected to a first conduit 656 that is connected at its other end to the diluent source 650 and the second leg 663 of the first T connector 660 is connected to a connector conduit (tubing) 652 that is connected at its other end to the first leg of the second T connector 662 associated with the second syringe 634. A main body 665 of the first T connector 660 is mated with the open end 636 of the first syringe 632 and defines a flow path thereto. The connector conduit 652 thus serves to fluidly connect the first and second syringes 632, 634. As previously mentioned, the valve mechanism 670 is preferably of the type that includes three independently operable valve elements with one associated with one leg 661, one associated with the other leg 663 and one associated with the main body 665.

With respect to the second T connector 662, a first leg 667 is connected to the connector conduit 652 and a second leg 669 is connected to a second conduit 658 that is connected to the main conduit 620 or can actually be simply one end of the main conduit. A main body 671 of the second T connector 662 is mated with the open end 636 of the second syringe 634. As with the first T connector 660, the second T connector 662 includes an internal valve mechanism 670 that is preferably of the type that includes three independently operable valve elements with one associated with one leg 667, one associated with the other leg 669 and one associated with the main body 671.

Figure 11:
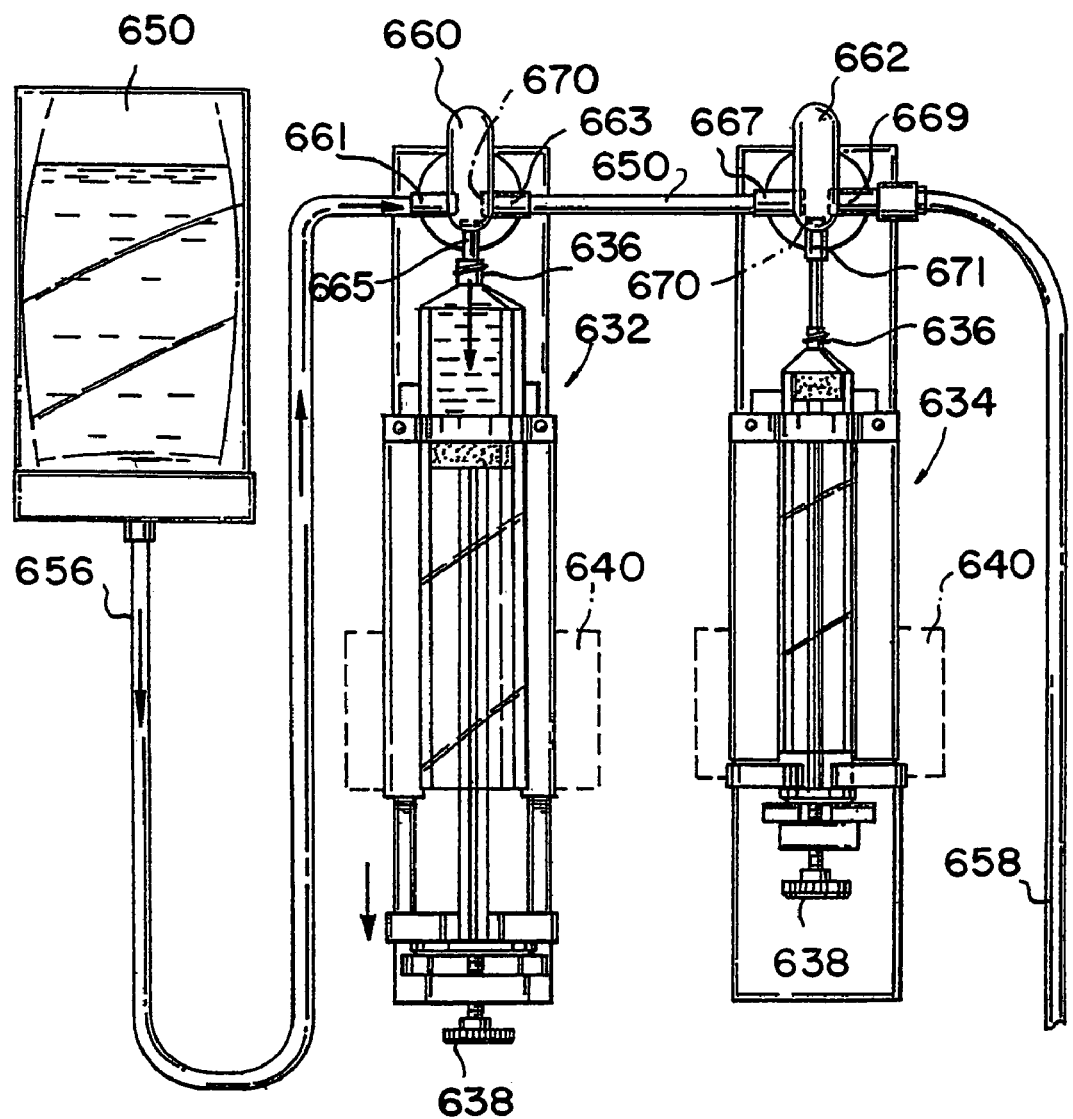
FIG. 11 is a side elevation view of a fluid pump system that is located in the fluid transfer area shown in a one operating position.

The operation of the fluid pump system 630 is now described with reference to FIGS. 2 and 11. If the operation to be performed is a reconstitution operation, the valve 670 associated with the second leg 669 is first closed so that the communication between the syringes and the main conduit 620 is restricted. The valve element 670 associated with first leg 661 of the T connector 660 is left open so that a prescribed amount of diluent can be received from the source 650. The valve element associated with the second leg 663 of the T connector 660 is initially closed so that the diluent from the diluent source 650 is initially drawn into the first syringe 630 and the valve element associated with the main body 665 is left open so that the diluent can flow into the first syringe 632. The driver 640 associated with the first syringe 632 is then actuated for a prescribed period of time resulting in the plunger 638 thereof being extended a prescribed distance. As previously mentioned, the distance that the driver 640 moves the corresponding plunger 638 is directly tied to the amount of fluid that is to be received within the syringe 632. The extension of the plunger 638 creates negative pressure in the first syringe 632, thereby causing diluent to be drawn therein.

Once the prescribed amount of fluid is received in the first syringe 632, the valve element associated with the main body 665 of the T connector 660 is closed and the valve element associated with the second leg 663 is open, thereby permitting flow from the first T connector 660 to the second T connector 662. At the same time, the valve element associated with the first leg 667 and the main body 671 of the second T connector 662 are opened (with the valve element associated with the second leg 669 being kept closed).

The driver 640 associated with the second syringe 634 is then actuated for a prescribed period of time resulting in the plunger 638 thereof being extended a prescribed distance which results in a precise, prescribed amount of fluid being drawn into the second syringe 634. The extension of the plunger 638 creates negative pressure within the barrel of the second syringe 634 and since the second T connector 662 is in fluid communication with the diluent source 650 through the first T connector 660 and the connector conduit 652, diluent can be drawn directly into the second syringe 632. The diluent is not drawn into the first syringe 660 since the valve element associated with the main body 665 of the first T connector 660 is closed.

Thus, at this time, the first and second syringes 632, 634 hold in total at least a prescribed volume of diluent that corresponds to at least the precise volume that is to be discharged through the cannula 520 into the vial 300 to reconstitute the medication contained therein.

It will be understood that all of the conduits, including those leading from the source 650 and to the cannula are fully primed with diluent prior to performing any of the above operations.

To discharge the prescribed volume of diluent into the vial, the process is essentially reversed with the valve 670 associated with the first leg 661 of the T connector 660 is closed to prevent flow through the first conduit 656 from the diluent source 650. The valve element associated with the second leg 669 of the second T connector 662 is opened to permit fluid flow therethrough and into the second conduit 658 to the cannula 520. The diluent that is stored in the first and second syringes 632, 634 can be delivered to the second conduit 658 in a prescribed volume according to any number of different methods, including discharging the diluent from one of the syringes 632, 634 or discharging the diluent from both of the syringes 634. For purpose of illustration only, it is described that the diluent is drawn from both of the syringes 632, 634.

The diluent contained in the first syringe 632 can be introduced into the main conduit 620 by opening the valve associated with the second leg 663 and the main body 665 of the first T connector 660 as well as opening up the valve element associated with the first leg 667 of the second T connector 662, while the valve element associated with the main body 671 of the second T connector 662 remains closed. The valve element associated with the second leg 669 remains open. The driver 640 associated with the first syringe 632 is operated to retract the plunger 638 causing a positive pressure to be exerted and resulting in a volume of the stored diluent being discharged from the first syringe 632 into the connector conduit 652 and ultimately to the second conduit 658 which is in direct fluid communication with the cannula 520. The entire volume of diluent that is needed for the reconstitution can be taken from the first syringe 632 or else a portion of the diluent is taken therefrom with an additional amount (fine tuning) to be taken from the second syringe 634.

When it is desired to withdraw diluent from the second syringe 634, the valve associated with the first leg 667 of the second T connector 662 is closed (thereby preventing fluid communication between the syringes 632, 634) and the valve associated with the main body 671 of the second T connector 662 is opened. The driver 640 associated with the second syringe 634 is then instructed to retract the plunger 638 causing a positive pressure to be exerted and resulting in the stored diluent being discharged from the second syringe 634 into the second conduit 658. Since the second conduit 658 and the main conduit 620 are fully primed, any new volume of diluent that is added to the second conduit 658 by one or both of the first and second syringes 632, 634 is discharged at the other end of the main conduit 620. The net result is that the prescribed amount of diluent that is needed to properly reconstitute the medication is delivered through the cannula 520 and into the vial 300. These processing steps are generally shown in the Figures in which the cannula 520 pierces the septum of the vial and then delivers the diluent to the vial and then the cannula unit 590 and the vial gripper device 530 are inverted to cause agitation and mixing of the contents of the vial.

It will be understood that in some applications, only one of the first and second syringes 632, 634 may be needed to operate to first receive diluent from the diluent source 650 and then discharge the diluent into the main conduit 520.

After the medication in the vial 300 has been reconstituted as by inversion of the vial and mixing, as described herein, the fluid pump system 630 is then operated so that a prescribed amount of medication is aspirated or otherwise drawn from the vial 300 through the cannula 520 and into the main conduit 620. Before the fluid is aspirated into the main conduit 620, an air bubble is introduced into the main conduit 620 to serve as a buffer between the diluent contained in the conduit 620 to be discharged into one vial and the aspirated medication that is to be delivered and discharged into one syringe 10. It will be appreciated that the two fluids (diluent and prepared medication) can not be allowed to mix together in the conduit 620. The air bubble serves as an air cap in the tubing of the cannula and serves as an air block used between the fluid in the line (diluent) and the pulled medication. According to one exemplary embodiment, the air block is a $\frac{1}{10}$ ml air block; however, this volume is merely exemplary and the size of the air block can be varied.

The aspiration operation is essentially the opposite of the above operation where the diluent is discharged into the vial 300. More specifically, the valve 670 associated with the first leg 661 of the first T connector 660 is closed and the valve associated with the second leg 669 of the second T connector 662 is opened to permit flow of the diluent in the main conduit into one or both of the syringes 632, 634. As previously mentioned, the second syringe 634 acts more as a means to fine tune the volume of the fluid that is either to be discharged or aspirated.

The drivers 640 associated with one or both of the first and second syringes 632, 634 are actuated for a prescribed period of time resulting in the plungers 638 thereof being extended a prescribed distance (which can be different from one another). As previously mentioned, the distance that the drivers 640 move the corresponding plungers 638 is directly tied to the volume of fluid that is to be received within the corresponding syringe 632, 634. By extending one or both of the plungers 638 by means of the drivers 640, a negative pressure is created in the main conduit 620 as fluid is drawn into one or both of the syringes 632, 634. The creation of negative pressure within the main conduit 620 and the presence of the tip end of the cannula 520 within the medication translates into the medication being drawn into the cannula 520 and ultimately into the main conduit 620 with the air block being present therein to separate the pulled medication and the fluid in the line.

It will be appreciated that the aspiration process can be conducted so that fluid is aspirated into one of the syringes 632, 634 first and then later an additional amount of fluid can be aspirated into the other syringe 632, 634 by simply controlling whether the valves in the main bodies 665, 671 are open or closed. For example, if fluid is to be aspirated solely to the first syringe 632, then the valve elements associated with the first and second legs 667, 669 of the second T connector 662 and the valve element associated with the second leg 663 and main body 665 of the first T connector 660 are all open, while the valve elements associated with the first leg 661 of the T connector 660 and the main body 671 of the T connector 662 remain closed. After a sufficient volume of fluid has been aspirated into the first syringe 632 and it is desired to aspirate more fluid into the second syringe 634, then the valve element associated with the first leg 667 simply needs to be closed and then the driver 640 of the second syringe 634 is actuated to extend the plunger 638.

Figure 9:
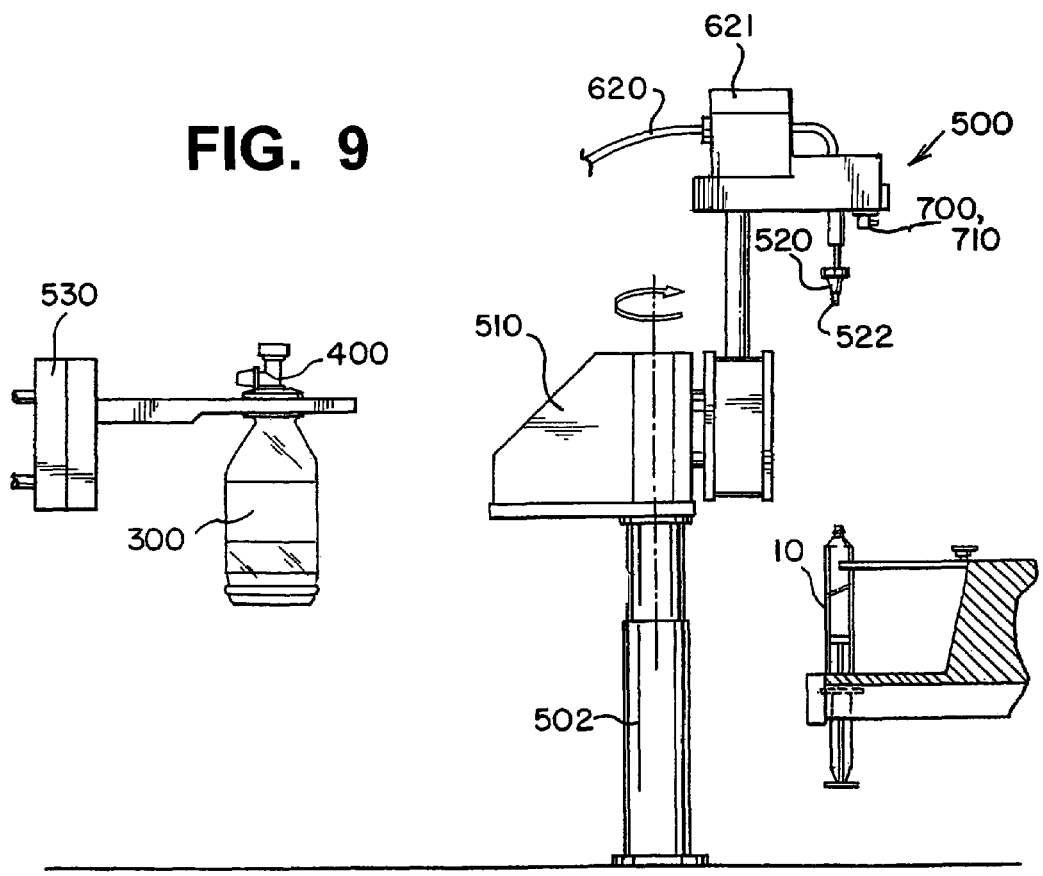
FIG. 9 is a side elevation view of the fluid transfer device in another position in which the fluid delivery system is rotated to the rotary dial that contains the nested syringes.
Figure 10:
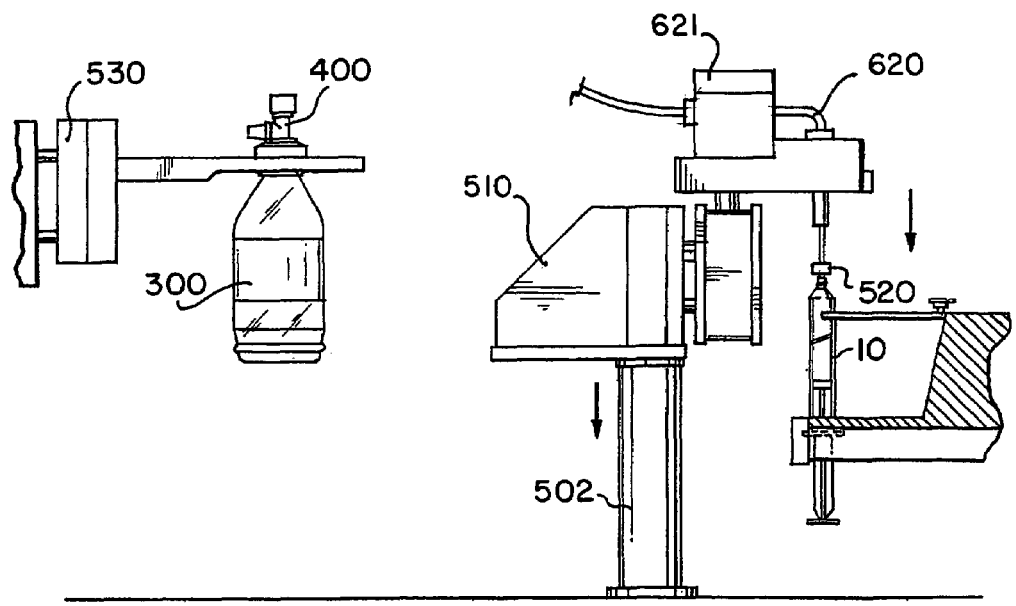
FIG. 10 is a side elevation view of the fluid transfer device in a subsequent position in which the fluid delivery system is retracted so that a cannula or the like thereof is inserted into the syringe to permit the aspirated unit dose of medication to be delivered to the syringe.

After aspirating the medication into the main conduit 620, the fluid transfer device 580 is rotated as is described below to position the cannula 520 relative to one syringe 10 that is nested within the rotary dial 130 as shown in FIG. 9. Since the plungers 638 are pulled a prescribed distance that directly translates into a predetermined amount of medication being drawn into the main conduit 620, the plungers 638 are simply retracted (moved in the opposite direction) the same distance which results in a positive pressure being exerted on the fluid within the main conduit 620 and this causes the pulled medication to be discharged through the cannula 520 and into the syringe 10. During the aspiration operation and the subsequent discharge of the fluid, the valves are maintained at set positions so that the fluid can be discharged from the first and second syringes 632, 634. As the plungers 638 are retracted and the pulled medication is discharged, the air block continuously moves within the main conduit 620 toward the cannula 520. When all of the pulled (aspirated) medication is discharged, the air block is positioned at the end of the main conduit signifying that the complete pulled medication dose has been discharged; however, none of the diluent that is stored within the main conduit 620 is discharged into the syringe 10 since the fluid transfer device 580, and more particularly, the drivers 640 thereof, operates with such precision that only the prescribed medication that has been previously pulled into the main conduit 620 is discharged into the vial 300. The valve elements can be arranged so that the plungers can be retracted one at a time with only one valve element associated with the main bodies 665, 671 being open or the plungers can be operated at the same time.

It will be appreciated that the fluid transfer device 580 may need to make several aspirations and discharges of the medication into the vial 300 in order to inject the complete prescribed medication dosage into the vial 300. In other words, the cannula unit 590 can operate to first aspirate a prescribed amount of fluid into the main conduit 620 and then is operated so that it rotates over to and above one syringe 10 on the rotary dial 130, where one incremental dose amount is discharged into the vial 300. After the first incremental dose amount is completely discharged into the syringe 10, the vertical base section 582 is rotated so that the cannula unit 590 is brought back the fluid transfer position where the fluid transfer device 582 is operated so that a second incremental dose amount is aspirated into the main conduit 620 in the manner described in detail hereinbefore. The vertical base section 582 is then rotated again so that the cannula unit 590 is brought back to the rotary dial 130 above the syringe 10 that contains the first incremental dose amount of medication. The cannula 520 is then lowered so that the cannula tip is placed within the interior of the syringe 10 and the cannula unit 590 (drivers 640) is operated so that the second incremental dose amount is discharged into the syringe 10. The process is repeated until the complete medication dose is transferred into the syringe 10.

Once the syringe 10 receives the complete prescribed medication dose, the vial 300 that is positioned at the fluid transfer position can either be (1) discarded or (2) it can be delivered to a holding station where it is cataloged and held for additional future use. More specifically, the holding station serves as a parking location where a vial that is not completely used can be used later in the preparation of a downstream syringe 10. In other words, the vials 60 that are stored at the holding station are labeled as multi-use medications that can be reused. These multi-use vials 60 are fully reconstituted so that at the time of the next use, the medication is only aspirated from the vials 60 as opposed to having to first inject diluent to reconstitute the medication.

Figure 6:
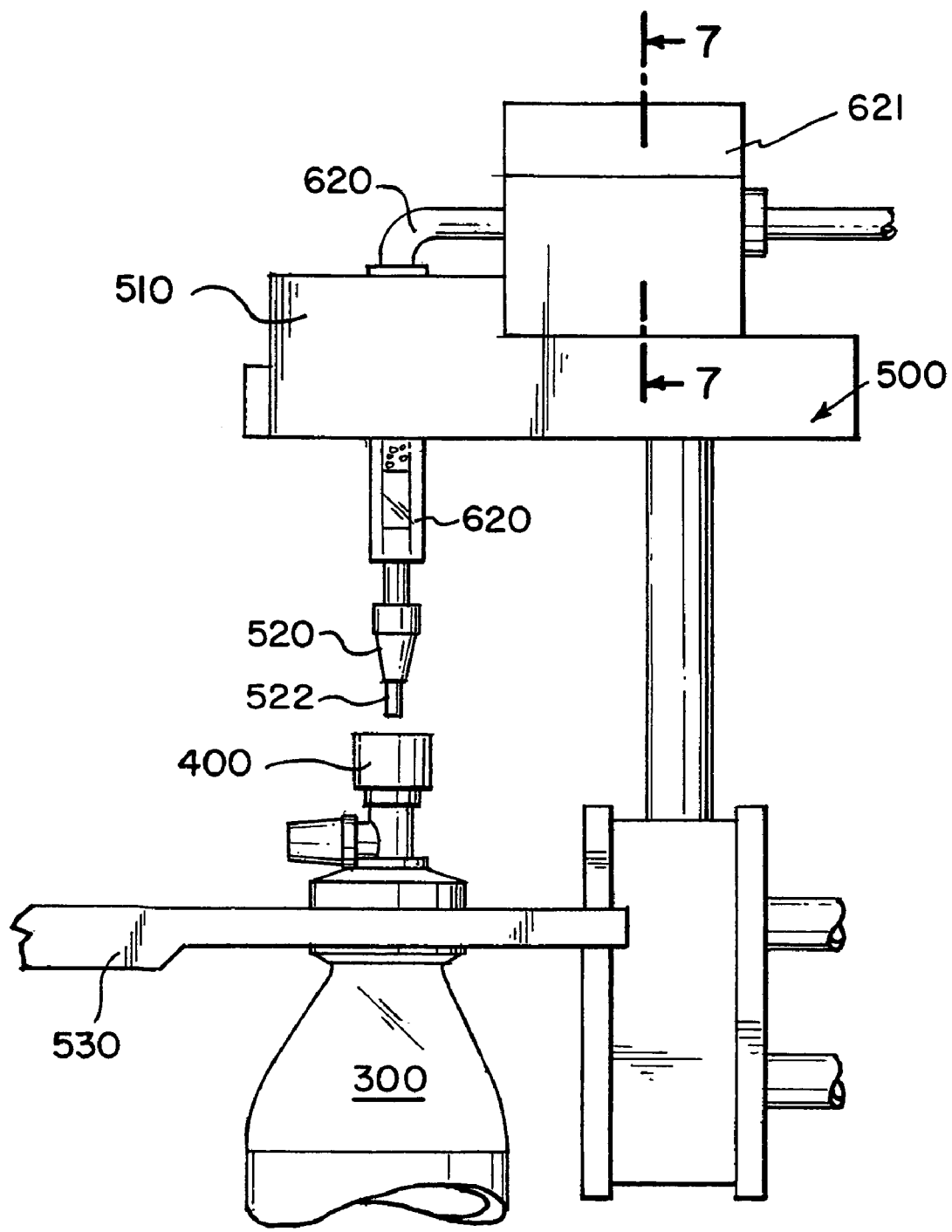
FIG. 6 is a side elevation view of the fluid delivery system retracted from the vial as well as a vision detection system for detecting the presence of unwanted foreign matter in an aspirated unit dose of medication.
Figure 7:
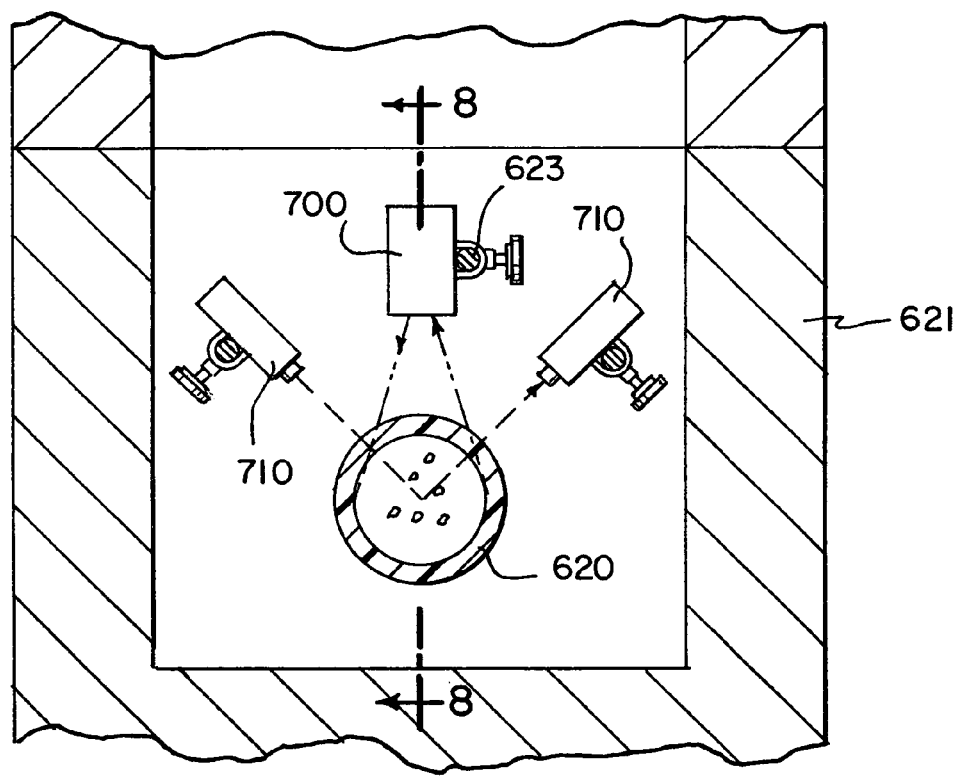
FIG. 7 is a cross-sectional view taken along the line 7-7 of FIG. 6.
Figure 8:
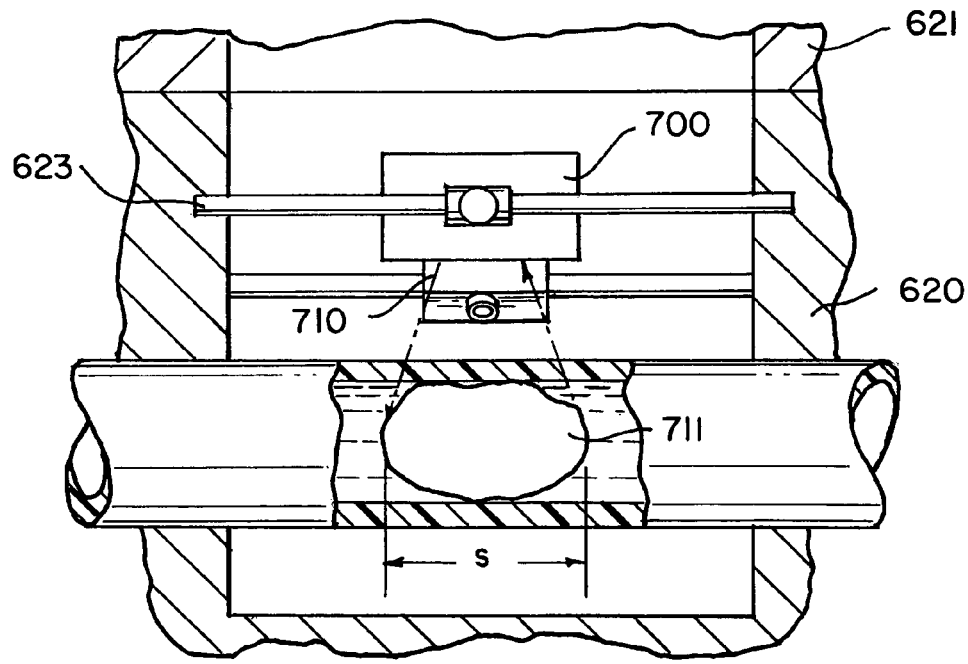
FIG. 8 is a cross-sectional view taken along the line 8-8 of FIG. 7.

According to the present invention, a safety feature is provided for monitoring and observing the quality of the medication that is aspirated or otherwise removed from the drug vial 300 into the cannula 520 and the main conduit 620 and is later delivered to the syringe 10. More specifically, as the medication is withdrawn from the drug vial 300, foreign matter may be present and can be withdrawn along with the medication. For example, undissolved drug particles or other solid material can inadvertently be withdrawn from the drug vial 300 and into the main conduit 620. The safety feature and integrity check system is best shown in FIGS. 6-8.

During a normal aspiration process, air bubbles can typically be formed as the liquid medication is withdrawn through the cannula 520 and into the main conduit 620, which is typically in the form of tubing or the like. These air bubbles are merely by-products that can be formed during the aspiration process; however, they are not foreign matter that contaminates the aspirated drug that is to be delivered to a syringe for later use by a patient. Thus, the safety feature should be able to discern between the presence of air bubbles compared to the presence of unwanted foreign matter, such as undissolved drug particles and other particles, such as pieces of the septum, etc.

While the safety feature can be incorporated into the cannula 520, it is preferably incorporated into the main conduit 620. For example, one exemplary safety feature is in the form of a first sensor 700 that is associated with either the cannula 520 or the main conduit and is constructed so that it is capable of detecting any unwanted foreign matter that may have been withdrawn from the drug vial 300 as the medication is aspirated. In the exemplary embodiment, the sensor 700 is mounted to the cannula housing 510 about the main conduit 620 such that when the cannula housing 510 is moved, the sensor 700 moves with it. For example, the sensor 700 itself can be attached to the cannula housing 510 via a bracket or the like that permits the sensor 700 to be positioned at the desired location relative to the conduit 620 where the aspirated medication is present during normal operation as it is aspirated into the main conduit 620 and as it is delivered through the main conduit 620 to the syringe 10. The sensor 700 should be able to differentiate an acceptable condition, such as the presence of air bubbles from an unacceptable condition, such as the presence of foreign matter, e.g., undissolved drug, small pieces of septum, etc. As shown in FIGS. 6-8, the sensor 700 can be disposed within a sensor and conduit locator structure 621 that serves to not only hold a length of the main conduit 620 in place but also serves as a mounting surface so that the sensor 700 can be mounted therein next to the main conduit 620. Preferably, the sensor 700 has some degree of travel within the structure 621 and this can be accomplished by any number of mechanisms. For example and according to one optional embodiment, the sensor 700 can slide along guide rails 623 (FIG. 8) so as to permit positioning and repositioning of the sensor 700 relative to the main conduit 700 and the cannula 520 itself. It will be appreciated that while the sensor 700 can travel within the structure 621, there is some type of locking mechanism associated therewith to allow the sensor 700 to be locked in a set position within the structure 621. Any number of conventional locking mechanisms can be used. The length of the main conduit 620 that extends through the structure 621 is fixed in place as by clamping two points of the main conduit 620, e.g., at the end walls of the structure 621, since it is desireable for the main conduit 620 not to move relative to the sensor 700 when performing the present sensing operation.

One exemplary sensor 700 that forms a part of the safety feature is disposed around the main conduit 620. For example, the sensor 700 can be disposed exterior and adjacent the main conduit 620. One type of sensor 700 is a photoelectric sensor that emits a light beam (visible or infrared) from its light-emitting element. There are several types of photoelectric sensors including a reflective type photoelectric sensor that is used to detect the light beam reflected from the target and a thrubeam type photoelectric sensor that is used to measure the change in light quantity caused by the target crossing the optical axis. More specifically, in the thrubeam type sensor, detection occurs when the target crosses the optical axis between a transmitter and a receiver. Some of the advantages of a thrubeam type sensor are: long-detecting distance; stable detecting position; opaque objects detectable regardless of shape, color or material; and it includes a powerful beam. In a diffuse-reflective type sensor, detection occurs when the light beam, emitted to the target, is reflected by the target and received. Some of the advantages of the diffuse-reflective type sensor are: it is a space-saving device (requires installation of sensor unit only); adjustment of optical axis is not required; reflective transparent objects are detectable; and color differentiation is possible. Other types of reflective sensors that are suitable for use include a definite-reflective sensor; a retro-reflective sensor, as well as any other type of sensor that is intended for detecting particles.

There are a number of different commercial suppliers for photoelectric sensors. A number of suitable photoelectric sensors are commercially available from Keyance Corporation. For example, one type of reflective sensor that is particularly suited for use in the present invention is commercially available under the trade name FU series sensors.

For example, the first sensor 700 can be configured so that light is directed into and through the main conduit 620 and the sensor 700 detects the presence of any particles by detecting any light beam reflected from the target, in this case a particle in the medication. The master controller of the present system is preferably configured so that when the first sensor detects that the light beam is reflected, a signal is generated and is delivered to the master controller which then further processes the signal to determine what operation should be taken. For example, if the light beam emitted from the sensor 700 strikes an object and is reflected back and received by the sensor unit, then the sensor 700 processes this as a detection of a foreign object (target) in the medication. In the event that the sensor 700 detects foreign matter, then the master controller can be configured to signal to the automated devices of the system that the medication within the main conduit 620 does not pass standards and therefore should be discarded, e.g., medication within the main conduit 620 can be discharged into a waste receptacle or the like.

It will also be appreciated that the master controller can be configured so that it is able to detect air bubbles that may be present in the main conduit when the medication is aspirated. In other words, a second sensor 710 can be configured and positioned near the main conduit 620 so that it detects and reflectance of the light beam due to the presence of air bubbles. In other words, a different second sensor 710 can be provided for the purpose of detecting air bubbles, indicated at 711 in FIG. 8, within the medication. Since air bubbles do not constitute unwanted foreign material, the first and second sensors 700, 710 and the master controller can be disposed around the main conduit 620 and integrated together so that a differentiation between air bubbles and solid particles can be made and therefore, if only air bubbles are present, the sensors send respective signals or no signals and the master controller reads and interprets the signals and will not instruct the automated device(s) to discard the aspirated medication since air bubbles are acceptable condition.

In other words, one preferred spot for mounting the sensors 700, 710 relative to the main conduit 620 is at a location where the sensors are close the cannula 500 at a distal location of the main conduit 620 since this location is generally a location at which early monitoring of the fluid (unit dose) within the main conduit 620 can be achieved.

For example, in one exemplary embodiment, the first sensor 700 is a diffuse-reflective sensor that is commercially available from Keyance Corporation under the trade name FU-66 as well as FZ-35 which are both sensitive sensors that are capable of detecting small particles on the order of 50 micron. Due to the high sensitivity of the sensor 700, it is capable of detecting both air bubbles and particles; however, it is not capable of differentiating between the two types of particles. More specifically and as a result of the high sensitivity, the readings of the FU-66 or FZ-35 sensor can be corrupted by the presence of some air bubbles inside the drug. Although, the air bubble is transparent to the light, in some uncommon conditions and depending upon the shape of the bubble, it is possible for the first sensor 700 to give a positive error as if a particle (foreign matter) is present. In order to filter out these false detections, another fiber optic sensor (e.g., FU-95Z) is used along with the diffusive-reflective sensor (e.g., FU-66 or FZ-35). The second sensor is a definite-reflective sensor and is capable of sensing small bubbles. The second sensor 710 is disposed alongside the first sensor 700 and the set-up of the two in combination enables the system to detect particles attached to air bubbles as well. As shown in FIG. 7, the second sensor 710 is arranged adjacent the first sensor 700 such that the emitted beam of the first sensor 700 is not detected by the second sensor 710 and vice versa. Thus, the exemplary second sensor 710 can be of the type shown in FIG. 7 and be formed of a light-emitting element and a light-receiving element that is arranged at a predetermine angle such that it is off-set therefrom. For example, the light-emitting element and the light-receiving element are off-set about 45 degrees from one another with the first sensor 700 being disposed between these two elements. Thus, any beam that is reflected off of an air bubble is received by the light-receiving element in its offset position. While this is one exemplary arrangement scheme between the first and second sensors 700, 710, it will be appreciated that there are a number of other arrangement that are possible so long as the false positives are not created due to light beams of one sensor being detected by the other sensor in the absence of any particles.

In order to detect the foreign matter that may have been aspirated, both of the sensors 700, 710 are preferably positioned at or very close to where the main conduit 620 is fluidly connected to the cannula 500 so as to sense and monitor the fluid contained within the main conduit 620. Air bubbles 711 that may be present are likely found in the same region of the main conduit 620 and this location, importantly, permits the fluid (unit dose) within the main conduit 620 to be analyzed as it is aspirated into the main conduit 620 through the cannula 500, as it stored therein, and as it is delivered to the syringe 10 back through the cannula 500.

Accordingly, the optical sensor is thus capable of detecting foreign unwanted matter that is present within the main conduit 620 along with the aspirated medication by detecting that the reference light beam is reflected and then received by the sensor. It will be appreciated that in most typical situations, air bubbles will not obstruct or reflect the reference light beam since they are not opaque in nature and therefore, they permit the reference light beam to pass through without any reflection back to the sensor unit.

Thus, any solid matter, including undissolved drug or pieces of the septum 320, that is present in the medication can be detected as a result of the reflection of the reference beam. Once the sensor detects that the reference beam is being reflected by some object, the sensor signals the master controller to take the necessary steps. For example, the medication can be discarded by discharching the medication into a waste drain 800 or the like and then the medication preparation process can be repeated and another prescribed dosage of medication can be aspirated into the main conduit 620.

It will also be understood that any number of other types of devices can be used as sensing devices so long as the sensors are capable of detecting the presence of unwanted solid foreign matter, such as undissolved solid drug or pieces of foreign material. Most of these sensors will employ some type of vision system that is capable of reading and determining whether opaque, foreign matter is present within the medication. For example, occlusion of a light beam can be detected as opposed to reflection thereof as described above.

Preferably, the sensor is disposed relative to the main conduit 620 so that the sensor monitors the condition of the meniscus of the aspirated medication, and more particularly, the sensor detects the presence of any foreign matter in the medication at the meniscus portion thereof. It will be appreciated that the sensor 700 can be moved and positioned relative to the main conduit 620 at a location other than the meniscus so that the sensor 700 can monitor for the presence of unwanted foreign matter in other locations along the main conduit 620.

While the detector has been at least partially described as being a sensor unit that is disposed around the main conduit 620, the sensor can come in other forms and be located in different locations depending upon the type of unit that is being used as a sensor. For example, the sensor can be in the form of a strip or the like that can be disposed around the main conduit 620. However, the location of the sensor unit should be controlled so that the emitted light beam does not strike a background and generate a false positive.

Accordingly, the sensor arrangement disclosed herein serves as a safety feature that is capable of detecting an undesirable condition, namely the presence of small solid particles in the aspirated unit dose of medication. By detecting this condition prior to delivery of the medication to the syringe, safety is ensured and cost savings result.

In yet another aspect, the detection system (e.g., sensors) can be linked to a communications network so that the detection system (or parts thereof) can be signaled from remote locations. For example, the sensor of the detection system can have a communications port that is in communication with a remote controller. An individual at a remote site can use the remote controller and signal any sensor to go offline. Conventional signal addressing protocol can be used so that the remote controller can be used to control a number of detection systems that are located in different places but all linked to the communications network. This permits the detection system to be by-passed when conditions require such action or for other reasons when it may be desirable to disable the detection system.

The present system and method for automating the medication preparation process and more specifically, the safety feature thereof serves as a cost reducing feature that is capable of detecting unwanted foreign matter that may be present in a unit dose of medication that is withdrawn from a drug vial. This not only increases safety patient since medication with potentially harmful foreign matter is not delivered to a patient but it also reduces the overall cost of the medication preparation system.

In yet another aspect of the present invention, the automated system includes a safety and cost reducing feature that is capable of detecting whether an underfill condition exists within the product container. More specifically, the medication is typically injected into the product container under action of a delivery device, such as a pump, and the underfill detection device is capable of calculating the total time that air or medication has been dispensed into the product container and based on this information, the device is able to measure the amount of the unit dose of medication within the product container and if necessary, additional medication can be added if it is determined that an underfill condition exists.

More specifically and in accordance with this embodiment, the controller is configured such that during a vial mode in which the unit dose of medication is prepared and transferred to the product container with a transfer device, the controller is operatively and communicatively linked to the sensors 700, 710 to perform the above operations as described above. In one embodiment, the sensors 700, 710 are orientated such that they are proximate the rotary dial 130 and the syringe 10 that is held therein such that the sensors 700, 710 are capable of detecting the presence of foreign matter and more importantly one or more air bubbles in the aspirated medication dose as the dose is discharged into the syringe 10 (product container). The presence and amount of undesirable air in the aspirated medication dose can be detected during the aspiration and delivery of the medication dose to the product container since the inner diameter of the tubing (main conduit 620) is a known parameter and the other parameters necessary to compute the volume of air can be determined. More specifically, the distance (s) of the air bubble(s), as measured within the tube, can be determined in accordance with the equation $s = v_1 \times t$, where s is the distance of the air bubble in the tube, where $v_1$ is the velocity of the fluid flow during the delivery of the aspirated dose to the product container and t equals the time elapsed between the beginning of detection of a bubble and the end of detection of a bubble by sensor 710. The distance "s" is shown in FIG. 8. In other words and as previously mentioned, the sensor 710 detects the presence of an air bubble and since it is operatively connected to the controller, the controller can detect the elasped time that the sensor 710 detects air in the line (main conduit 620) as the dose is being aspirated into the main conduit 620 and/or is being discharged into the product container.

It will be appreciated that an aspirated dose of medication may contain more than one air bubble and therefore, the controller must be configured so that it can sum up the total elapsed time that the sensor 710 detects the presence of air in the line. The parameter (t) is thus a sum of each elasped time that the sensor 710 detects air in the line. Once the parameter (t) is known and the parameter (vi) is known since the pumping system has an associated pumping speed (fluid flow rate), these two values can be multiplied together to arrive at the distance (s) (i.e., as measured between a starting point and end point) of the air bubble(s) in the line. It does not matter whether this value (s) is a product of one air bubble in the line or is a sum of multiple air bubbles since in both cases, the air bubbles merely take up volume in the line that should instead be occupied by the medication. This value (s) is thus the total length of dead space in the line.

Once the controller calculates the total length (s) of dead space in the line that is occupied by air, the controller then calculates the volume of the air in the line as a product of the total length of dead space (air) in the line and the inner diameter of the line (tubing). As is known, the volume (v) can be calculated by the equation $v=[\pi d^2/4] \times (s)$, wherein d is the inner diameter of the main conduit 620 and (s) is the above described distance. Once the volume of dead space (air) is calculated, the controller then instructs the pumping system to delivery an additional amount of medication to the product container which is equal to the volume of dead space so as to compensate for the volume of air in the line. For example, if the desired medication dose that is to be delivered to the product container is 10 ml and as this medication dose is delivered to the product container, the controller calculates that air that occupies a volume of 1 ml is present in the line, then the controller instructs the pumping system to delivery an additional amount of medication to the product container to compensate for the air bubble(s). Of course, during the delivery of this additional amount of medication, the sensors 700, 710 operate and are in communication with the controller such that in the event that there is an air bubble(s) in the compensation volume of medication, the controller repeats the above steps and calculates the volume of dead space and then calculates a second compensation volume of medication that is to be added to the already delivered medication dose. This entire process is repeated until the medication dose that is delivered to the product container is equal to the desired, inputted medication dose volume.

It will be appreciated that the controller does not have to make the above calculations if the sensor 710 does not detect the presence of air in the line. In other words, in an optimal aspirated and delivery of the medication dose, the sensors 700, 710 detect neither foreign matter nor air bubbles in the medication dose and thus the dose is simply delivered to the product container, e.g., syringe. Thus, if no air bubbles are present in the aspirated dose of medication, the volume of the aspirated dose of medication will be equal to the volume of medication that is to be delivered to the product container, e.g., the syringe.

In terms of the construction of the controller, it will be appreciated that the controller can simply include an additional electronic board that is configured to perform the above operations. The controller can thus have an electronic board (PCB) that is associated with the pure detection of foreign matter and air bubbles and then a second electronic board that is associated with the second operation of calculating the total volume of air that is present in the line as it is delivered to the product container.

It will be understood that the sensors 700, 710 are continuously monitoring fluid in the main conduit 620 as it is first aspirated through the cannula 500 into the main conduit 620, as it is secondly stored in the main conduit 620 between cannula operations, and then thirdly, when it is delivered back through the cannul 500 to product container. This system thus ensures that if there is a change in conditions of the fluid within the main conduit 620 after it has been aspirated but prior to delivery to the product container and then when it is later delivered to the product container, the system is able to detect such a change. For example, an air bubble might not be present as the fluid is first aspirated by the sensors 700, 710 but then it later develops and therefore, as the fluid with the air bubble passes again by the sensors during delivery to the product container, the sensors will detect the presence of the air bubble.

The present system thus incorporates a feature in the form of sensor 710 which when used in combination with the controller is able to first determine when an underfill condition exists where the volume of the unit dose of medication is actually less than the prescribed volume of the unit dose that is to be dispensed into the product container. An underfill condition is not acceptable since the product container must contain the precise amount of medication that it is supposed to have and therefore, an underfill condition will result in the product container being rejected. By having a precise sensing mechanism and more importantly, having a system that can calculate the precise degree of the underfill condition, the present system can correct the underfill condition by delivering an amount of medication to the actual volume of medication in the product container so to compensate thereof and to make the actual volume of the medication in the product container equal to the prescribed volume of the unit dose of medication. By refilling the product container with just enough medication until the product container holds the prescribed volume of medication, under weight rejection of the product container is avoided. It will be appreciated that the automated system disclosed herein is merely exemplary in nature and that there are a number of other types of automated medication preparation systems that can be used in combination with the optical device of the preent invention so long as the optical device is capable of detecting air bubbles and the controller includes the necessary electronic boards to permit calculation of how much space the air bubble (s) occupy in the withdrawn unit dose of medication. Refill or "top off" additions of the medication are performed to ensure that the product container holds the precise amount of medication.

What is claimed is:

1. An automated medication preparation system including preparation and dispensing of medication to an individual product container and detection of any underfill condition where an insufficient amount of medication is delivered to the product container, the system comprising:

an automated device for preparing and dispensing a prescribed unit dose of medication;

a controller operatively connected to the automated device, the controller receiving a first input that represents a volume of the prescribed unit dose of medication that is to be delivered to the product container; and an optical device for detecting the underfill condition when the actual amount of the unit dose of medication that is delivered to the product container is less than the value of the first input and whereupon, if an underfill condition is detected, then the controller instructs the automated device to deliver medication to the product container until the amount of medication in the product container is equal to the inputted volume, wherein the optical device is configured to detect an object within the unit dose of medication that causes the underfill condition.

2. The automated system of claim 1, wherein the automated device comprises an automated syringe preparation that includes reconstitution of the medication and delivery of the unit dose of the reconstituted medication to a syringe from a drug vial, the automated device includes a fluid delivery device for delivering the prescribed unit dose of medication to the syringe in a just-in-time for use manner, wherein the fluid delivery device is adapted to aspirate the reconstituted medication into a main fluid conduit and later discharging reconstituted medication from the drug vial into the syringe.

3. The automated system of claim 2, wherein the fluid delivery device is fluidly connected to the main conduit that is selectively connected at its opposite end to the diluent source and to a means for creating either negative pressure or positive within the main conduit for aspirating fluid into the main conduit or discharging fluid therefrom, respectively and wherein the means comprises (1) a collection member for storing diluent received from either the diluent source or diluent that is drawn into the collection member from a downstream section of the main conduit; and (2) a control unit and a valve mechanism that are operatively connected to the collection member to create negative pressure therein to draw fluid therein or to create positive pressure to force fluid to be discharged therefrom.

4. The automated system of claim 3, wherein the collection member comprises:
a first syringe having a barrel with an interior having a first volume; and
a second syringe having a barrel with an interior having a second volume;
wherein each of the first and second syringes having a slideable plunger contained in the respective barrel and each syringe being in selective fluid communication with each of the diluent source and the main conduit that leads to the fluid delivery device.

5. The automated system of claim 4, wherein the control unit comprises:
a first syringe driver associated with the first syringe for selectively moving the plunger a prescribed distance;
a second syringe driver associated with the second syringe for selectively moving the plunger a prescribed distance; and
the valve mechanism includes a first valve for providing selective fluid communication between the control unit and the diluent source and a second valve for providing selective fluid communication between the control unit and the downstream section of the main conduit.

6. The automated system of claim 5, wherein the first and second syringes are fluidly interconnected by a connector conduit that has a valve associated therewith for permitting selective flow between the syringes.

7. The automated system of claim 5, wherein at least one of the first and second syringes has an input port and an output port with the input port being connected to a first conduit that connects at its opposite end to the diluent source with a valve being associated with the first conduit to provide selective communication between the diluent source and the input port, the output port being connected to a second conduit that connects at its opposite end to the main conduit with a valve being associated with the second conduit to provide selective communication between the output port and the main conduit.

8. The automated system of claim 5, wherein each of the first and second syringe drivers comprises a stepper motor that operates such that an incremental distance of movement of the plunger is equated to a number of steps through which the motor is driven, thereby permitting precise control over the exact distance that the plunger is moved.

9. The automated system of claim 1, further including a particulate sensor proximate a main fluid conduit to detect foreign matter present in the unit dose of medication, the main fluid conduit being part of the automated device and holds the unit dose of medication prior to delivery to the product container.

10. The automated system of claim 9, wherein the particulate sensor is a photoelectric sensor that detects any reflection of an emitted beam which is indicative of foreign matter being present in the unit dose of medication that is contained within the main fluid conduit.

11. The automated system of claim 10, wherein the particulate sensor includes a light-emitting element for producing the light beam and a light-receiving element for receiving any light beam that reflects off of the foreign matter, the particulate sensor generating and sending a signal to the controller if the particulate sensor detects the foreign matter.

12. The automated system of claim 9, wherein the particulate sensor is a diffusive-reflective sensor that is configured to detect particles as small as 50 micron, the light-emitting element and the light-receiving element being contained within a single housing that is positioned facing a main conduit.

13. The automated system of claim 12, wherein the particulate t sensor is configured and has a sensitivity such that it is capable of detecting air bubbles as well as the foreign matter in the form of solid particles.

14. The automated system of claim 1, wherein the optical device comprises a bubble sensor that comprises a photoelectric sensor that lacks sensitivity to detect minute particles but is capable of detecting air bubbles and generates a signal when air bubbles are detected, the signal being sent to the controller.

15. The automated system of claim 14, further comprising a particulate sensor to detect foreign matter present in the unit dose of medication, wherein the particulate sensor comprises a diffusive-reflective sensor that is capable of detecting both air bubbles and solid particles and the bubble sensor in combination with the particulate sensor forms a filter to filer out false positives that can result if the particulate sensor detects air bubbles as opposed to solid particles such that if a master controller in communication with both sensors and receives signals from both the particulate sensor and bubble sensor then the controller filters out the false positive and the aspirated unit dose of medication is delivered to the syringe.

16. The automated system of claim 1, wherein the optical device is configured such that it sends a signal if an air bubble is detected and the controller is in communication with the optical device and receives a second input and a third input, with the second input representing a flow rate of the unit dose of medication as it is delivered under action of the automated device, the third input representing an elapsed time period that the optical device detects air bubbles in the unit dose of medication, whereupon, the controller calculates a volume of the air bubbles in the unit dose of medication as a product of the second and third inputs, with the actual amount of the unit dose of medication that is delivered to the product container being the first input minus the volume of the air bubbles.

17. The automated system of claim 16, wherein there are more than one third input and the controller calculates the total elapsed time period as a sum of multiple third inputs.

18. The automated system of claim 16, wherein the controller calculates the volume of air bubbles as a product of an inner diameter of a main fluid conduit that receives and holds the unit dose of medication prior to delivery to the product container.

19. The automated system of claim 16, wherein the elapsed time period for each air bubble is a time period beginning with a starting point where the optical device detects the air bubble and ends with an ending point where the optical device no longer detects presence of the air bubble.

20. The automated system of claim 3, wherein the fluid delivery device is fluidly connected to the main conduit and to a means for creating negative or position pressure within the main conduit for aspirating fluid into the main conduit or discharging fluid therefrom, respectively.

21. The automated system of claim 20, wherein the fluid delivery device comprises at least one syringe for generating positive and negative pressure.

22. A method for automated preparation of a medication including automated preparation and dispensing of medication to an individual product container and detection of an underfill condition where an insufficient amount of medication is delivered to the product container comprising the steps of:
   providing an automated device for preparing and dispensing a prescribed unit dose of medication;
   operatively connecting a controller to the automated device;
   inputting a first value to the controller that represents a volume of the prescribed unit dose of medication that is to be delivered to the product container;
   providing an optical device for detecting the underfill condition when the actual amount of the unit dose of medication that is delivered to the product container is less than the inputted volume; and
   whereupon, if an underfill condition is detected, then the controller instructs the automated device to deliver medication to the product container until the amount of medication in the container is equal to the inputted volume.

23. A method of claim 22, further including the steps of:
   disposing a first sensor to detect foreign matter present in the unit dose of medication;
   detecting by means of the first sensor the presence of any foreign matter in the unit dose of medication; and
   delivering the unit dose of medication to the product container in a just-in-time manner if the unit dose of medication is free of foreign matter and whereupon, if foreign matter is detected, a signal is delivered to the controller and the unit dose of medication is prevented from being delivered to the product container.

24. The method of claim 23, wherein the step of detecting the presence of foreign matter comprises the steps of:
   emitting a light beam from the first sensor toward the unit dose of medication contained in a main fluid conduit that has been aspirated and is ready for delivery to the product container;
   detecting whether the light beam is reflected as a result of contacting foreign matter that is contained in the medication in the main fluid conduit; and
   if the light beam is reflected, then the signal is delivered to the controller and the unit dose of medication is prevented from being delivered to the product container.

25. The method of claim 23, further comprising the step of:
   differentiating between air bubbles and the foreign matter, wherein the first sensor only generates a signal instructing that the unit dose of medication be discarded if foreign matter is present in the medication as opposed to air bubbles.

26. The method of claim 23, wherein providing the optical device comprises the steps of:
   disposing a second sensor proximate the automated device, wherein the second sensor has a sensitivity that permits detection of air bubbles and not solid particles;
   emitting a light beam toward the unit dose of medication that is contained in a main fluid conduit;
   detecting whether the light beam is reflected and if so, generating an air bubble signal that is delivered to the controller; and
   processing signals from one or both of the first and second sensors with the master controller such that if the first sensor detects reflection of its emitted light beam and the second sensor detects reflection of its emitted light beam, then the controller determines the existence of a false positive and the reconstituted medication is delivered to the syringe.

27. The method of claim 22, further including the steps of:
   inputting a second input to the controller, the second input representing a flow rate of the unit dose of medication as it is delivered under action of the automated device;
   inputting a third input to the controller, the third input representing an elapsed time period that the optical device detects air bubbles in the unit dose of medication as the unit dose of medication is delivered to the product container by the automated device; and
   calculating with the controller a volume of the air bubbles in the unit dose of medication as a product of the second and third inputs, with the actual amount of the unit dose of medication that is delivered to the product container being the first input minus the volume of the air bubbles.

28. The method of claim 27, wherein there are more than one third input and the method includes the step of:
   calculating the total elapsed time period as a sum of plural third inputs.

29. The method of claim 22, further including the step of:
   calculating the volume of air bubbles based on an inner diameter of a main fluid conduit that receives and holds the unit dose of medication prior to delivery to the product container; and
   calculating an elapsed time period for each air bubble as being a time period beginning with a starting point where the optical device detects the air bubble and ends with an ending point where the optical device no longer detects the presence of the air bubble.

30. The method of claim 22, wherein the automated device is in selective fluid communication with a fluid pump apparatus that is in selective fluid communication with a diluent source, the fluid pump apparatus having a first controllable syringe that is in fluid communication with the diluent source and with a second controllable syringe that is also in selective fluid communication with the fluid delivery device through the main conduit which is primed, each of the syringes being operatively connected to a drive that causes either a positive or negative pressure to exist in a barrel thereof, and the step of reconstituting the medication includes the steps of:
   opening fluid communication between the diluent source and the first syringe and preventing fluid communication between the second syringe and the fluid delivery device;
   operating a drive of one of the first and second syringes to create a negative pressure therein resulting in a prescribed amount of diluent being drawn into the barrel thereof;

preventing fluid communication between the diluent source and the first syringe and allowing fluid communication between the second syringe and the delivery device;

operating the drive so as to discharge the prescribed amount of diluent from one of the first and second syringes into the primed main conduit resulting in the prescribed amount of diluent being discharged through the delivery device and into the vial;

agitating contents of the vial;

operating a drive of one of the first and second syringes to create a negative pressure therein resulting in the prescribed dosage amount of medication being aspirated into the main conduit with an air block separating the aspirated medication from the diluent in the main conduit due to a volume of diluent, which is equal to the prescribed dosage amount, be drawn into the syringe barrel;

positioning the delivery device within the syringe; and operating the drive of one of the first and second syringes to create a positive pressure therein resulting in the prescribed dosage amount of medication being discharged from the main fluid conduit into the syringe as a result of the volume of diluent being discharged from the syringe into the main conduit.

31. An automated medication preparation system including preparation and dispensing of medication to an individual product container and detection of any underfill condition where an insufficient amount of medication is delivered to the product container, the system comprising:

an automated device for preparing and dispensing a prescribed unit dose of medication;

a controller operatively connected to the automated device, the controller receiving a first input that represents a volume of the prescribed unit dose of medication that is to be delivered to the product container; and an optical device for detecting the underfill condition when the actual amount of the unit dose of medication that is delivered to the product container is less than the value of the first input and whereupon, if an underfill condition is detected, then the controller instructs the automated device to deliver medication to the product container until the amount of medication in the product container is equal to the inputted volume wherein the controller calculates a top off volume of medication that is delivered to the product container when an underfill condition is detected, the top off volume being an amount equal to the first input volume minus the actual amount of the unit dose that is delivered to the product container.

32. An automated medication preparation system including preparation and dispensing of medication to an individual product container and detection of any underfill condition where an insufficient amount of medication is delivered to the product container, the system comprising:

an automated device for preparing and dispensing a prescribed unit dose of medication;

a controller operatively connected to the automated device, the controller receiving a first input that represents a volume of the prescribed unit dose of medication that is to be delivered to the product container; and an optical device for detecting the underfill condition when the actual amount of the unit dose of medication that is delivered to the product container is less than the value of the first input and whereupon, if an underfill condition is detected, then the controller instructs the automated device to deliver medication to the product container until the amount of medication in the product container is equal to the inputted volume, wherein the optical device is configured to detect at least one condition selected from the group consisting of (a) particles being present in the unit dose of medication and (b) bubbles being present within the unit dose of medication.

* * * * *